(12) United States Patent  (10) Patent No.: US 8,016,804 B2
Lee                        (45) Date of Patent: Sep. 13, 2011

(54) HYGIENIC BAND HAVING THREE-DIMENSIONAL STRUCTURE AND MANUFACTURING METHOD THEREOF

(76) Inventor: Kyeng Im Lee, Gyeonggi-do (KR)

( * ) Notice: Subject to any disclaimer, the term of this patent is extended or adjusted under 35 U.S.C. 154(b) by 577 days.

(21) Appl. No.: 12/089,666

(22) PCT Filed: Oct. 13, 2006

(86) PCT No.: PCT/KR2006/004136
§ 371 (c)(1),
(2), (4) Date: Apr. 9, 2008

(87) PCT Pub. No.: WO2007/043836
PCT Pub. Date: Apr. 19, 2007

(65) Prior Publication Data
US 2008/0275413 A1   Nov. 6, 2008

(30) Foreign Application Priority Data
Oct. 13, 2005 (KR) ................ 10-2005-0096412

(51) Int. Cl.
A61F 13/15 (2006.01)
B29C 65/00 (2006.01)

(52) U.S. Cl. ....... 604/385.201; 604/385.01; 604/385.21; 604/385.16; 156/164; 156/204

(58) Field of Classification Search .......... 604/385.01, 604/385.201, 385.21, 385.16; 156/164, 204
See application file for complete search history.

(56) References Cited

U.S. PATENT DOCUMENTS

| 4,673,403 A | * | 6/1987 | Lassen et al. .......... 604/385.17 |
| 5,591,150 A | | 1/1997 | Olsen et al. |
| 5,919,181 A | | 7/1999 | Visscher et al. |

FOREIGN PATENT DOCUMENTS

| CN | 1152862 A | 6/1997 |
| CN | 2710598 Y | 7/2005 |
| EP | 0302523 | 2/1989 |
| JP | 62-111021 A | 7/1987 |
| JP | 64-070051 | 3/1989 |
| JP | 6-77724 | 11/1994 |

(Continued)

OTHER PUBLICATIONS

Office Action from Japan Patent Office regarding a Japanese counterpart application dated Aug. 4, 2010.

*Primary Examiner* — Jacqueline F Stephens
(74) *Attorney, Agent, or Firm* — Rabin & Berdo, P.C.

(57) ABSTRACT

Disclosed herein are a hygienic band having a three-dimensional structure and a manufacturing method thereof. The hygienic band is inserted naturally along a corresponding curved surface of a user's body to be in close contact with the body, thus improving her dressing style without affecting her health, and preventing menstrual blood from leaking along the curved surface of the body. The hygienic band has a pad having an absorbent layer and a cover. A rear folded part is provided at a central region on a rear portion of the pad, and has first and second folded surfaces, each having the shape of a triangle which is inclined such that a rear portion thereof is higher. When she wears the hygienic band, the rear folded part protrudes inwards in the shape of a triangular pyramid and is inserted to be in close contact with a curved surface of her body.

18 Claims, 8 Drawing Sheets

FOREIGN PATENT DOCUMENTS

| | | |
|---|---|---|
| JP | 3024411 A | 2/1996 |
| JP | 10-502843 T | 3/1998 |
| JP | 2001-509403 A | 7/2001 |
| JP | 2003-038553 | 2/2003 |
| KR | 1999-0033791 | 8/1999 |
| KR | 10-0244550 | 2/2000 |
| KR | 20-0214175 | 12/2000 |
| KR | 20-0214179 | 12/2000 |
| WO | WO-99/01095 | 1/1999 |
| WO | WO-02/085269 | 10/2002 |

* cited by examiner

[Fig. 1]
(a)
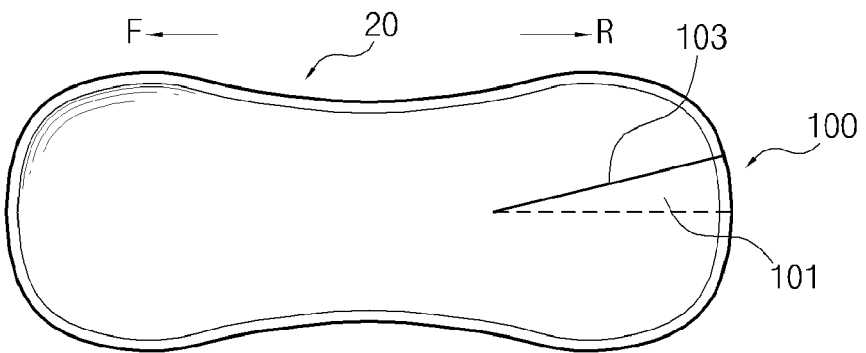
(b)
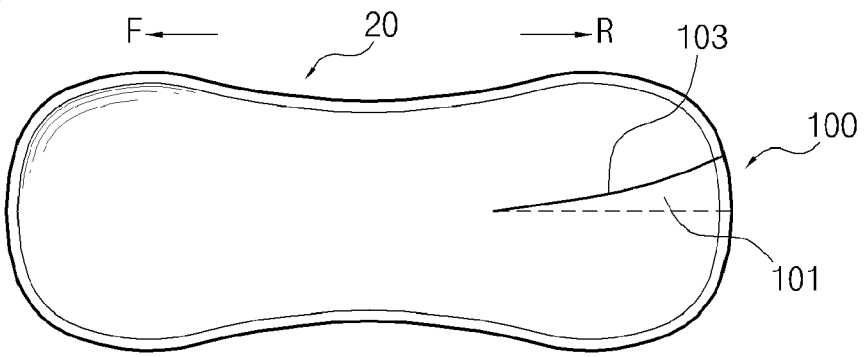
(c)
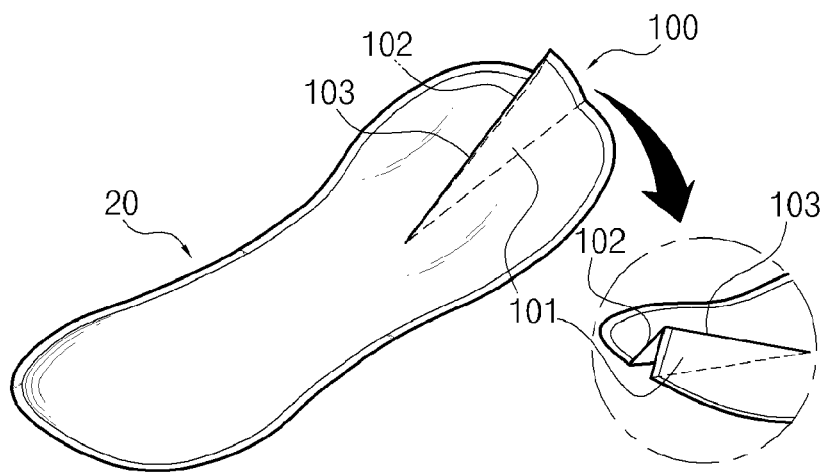

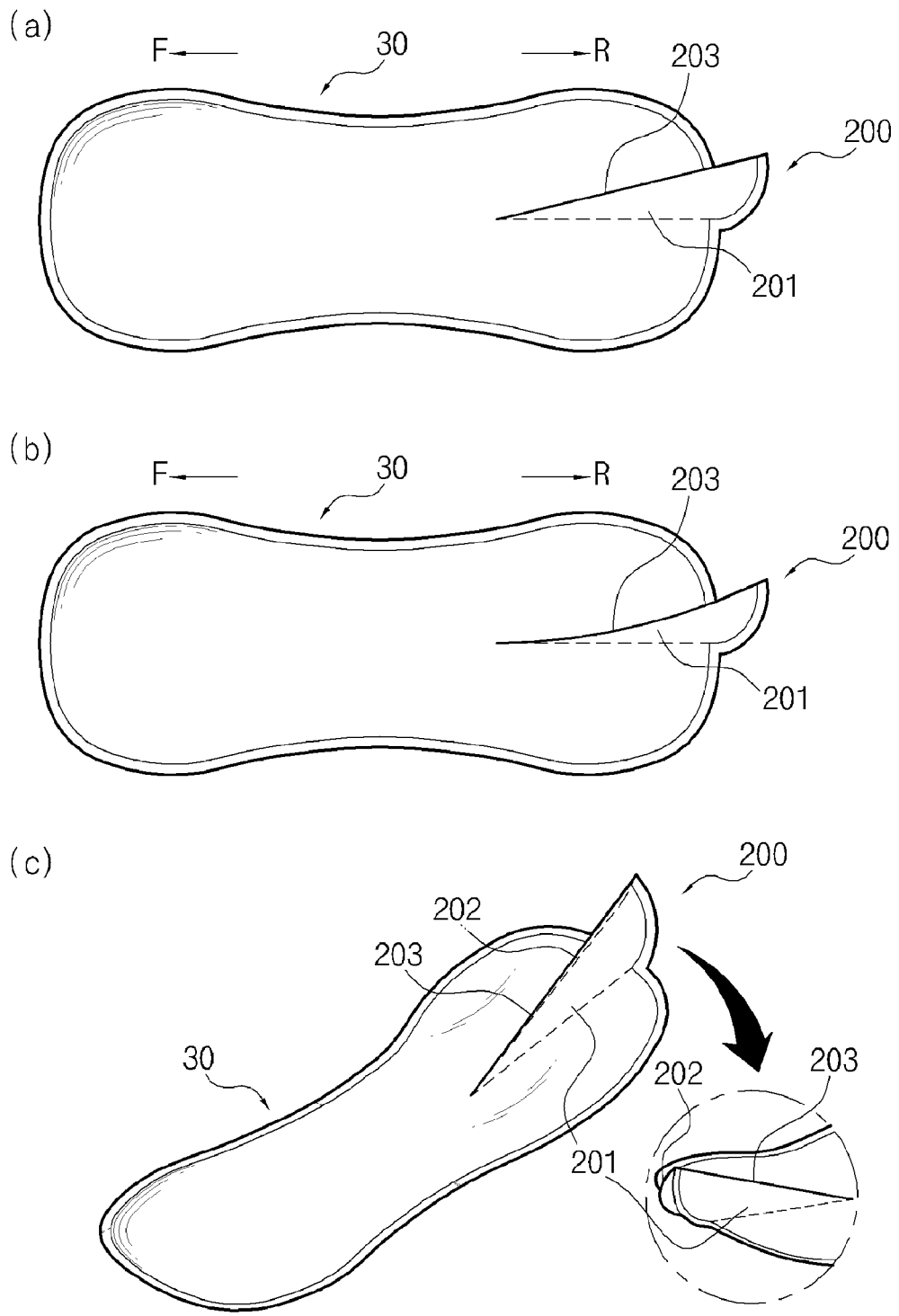
[Fig. 2]

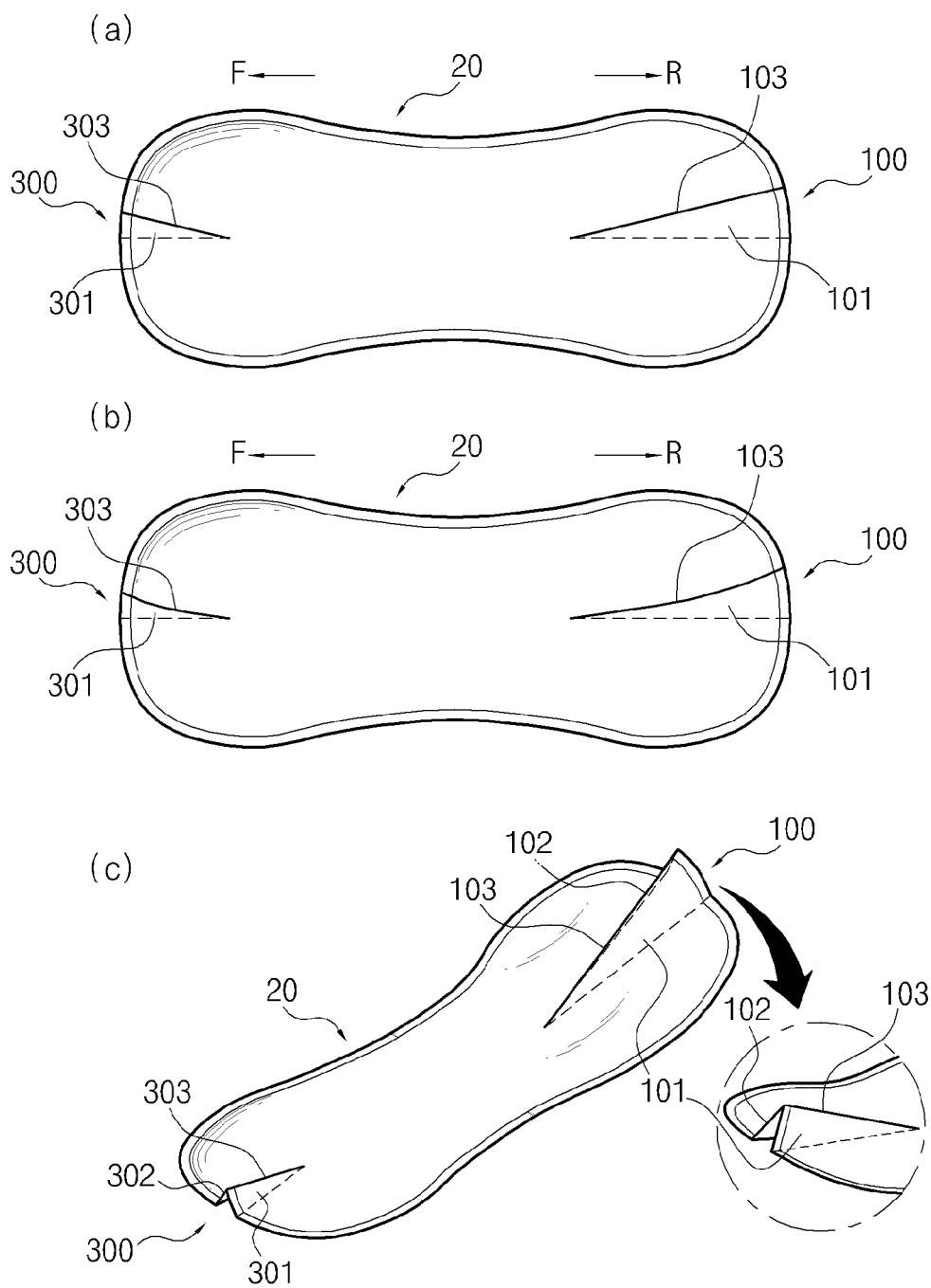

[Fig. 4]
(a)
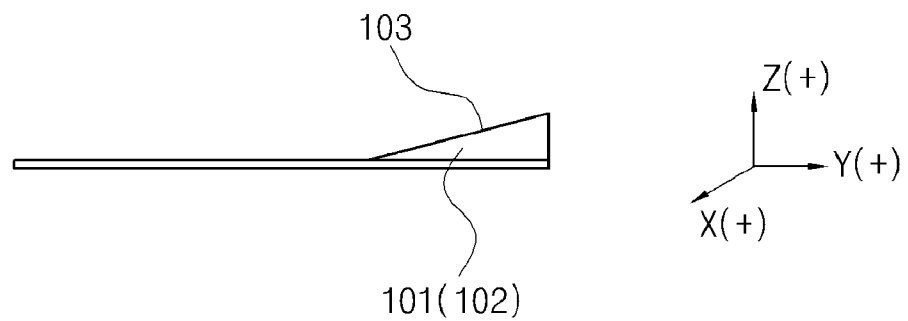
(b)
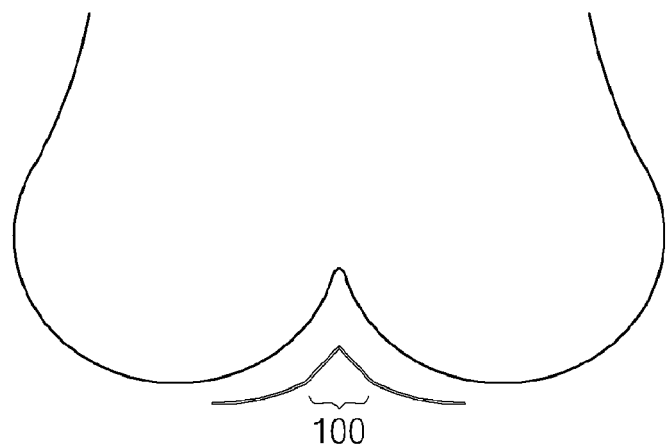
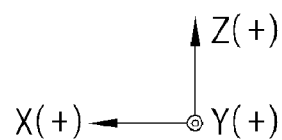

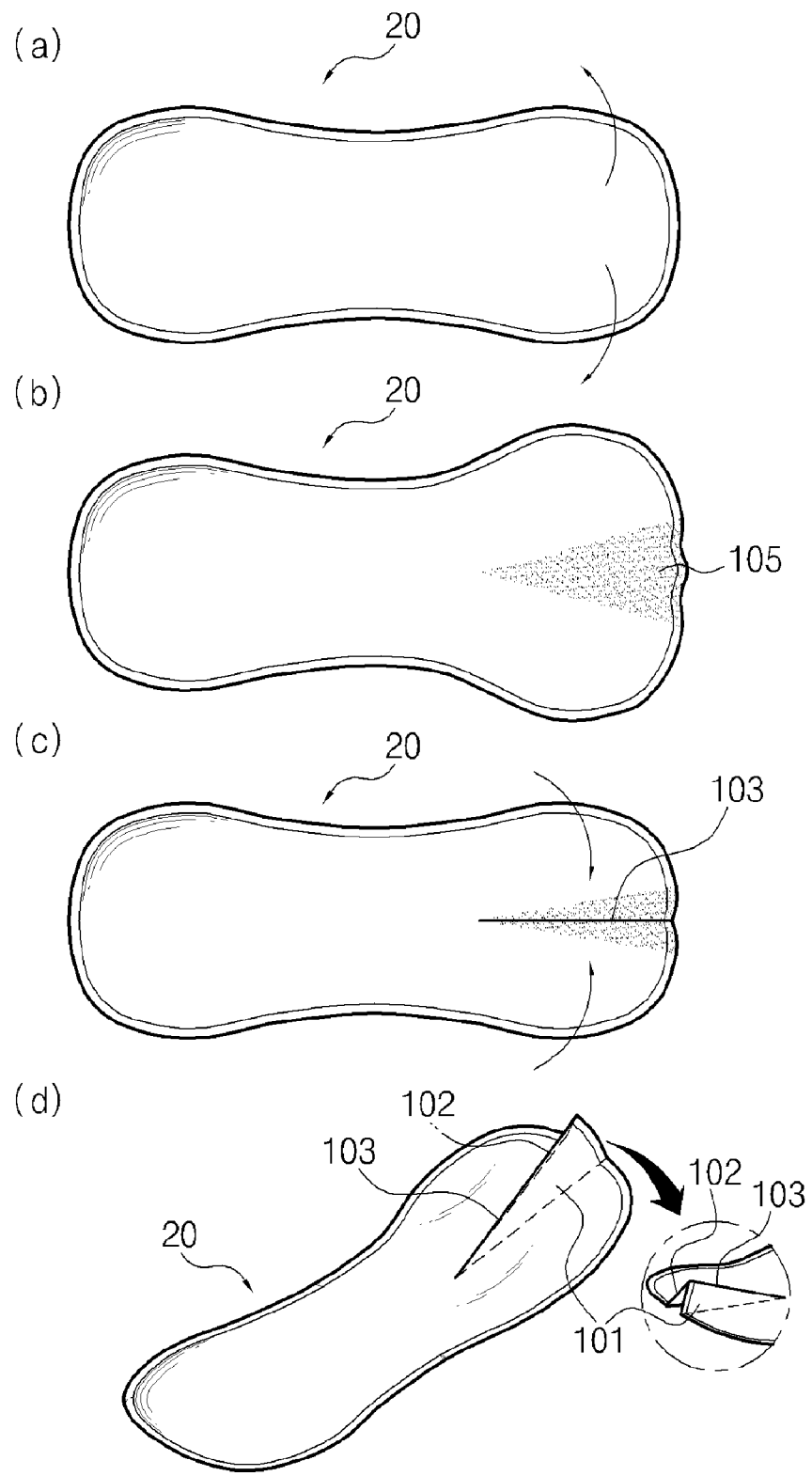
[Fig. 5]

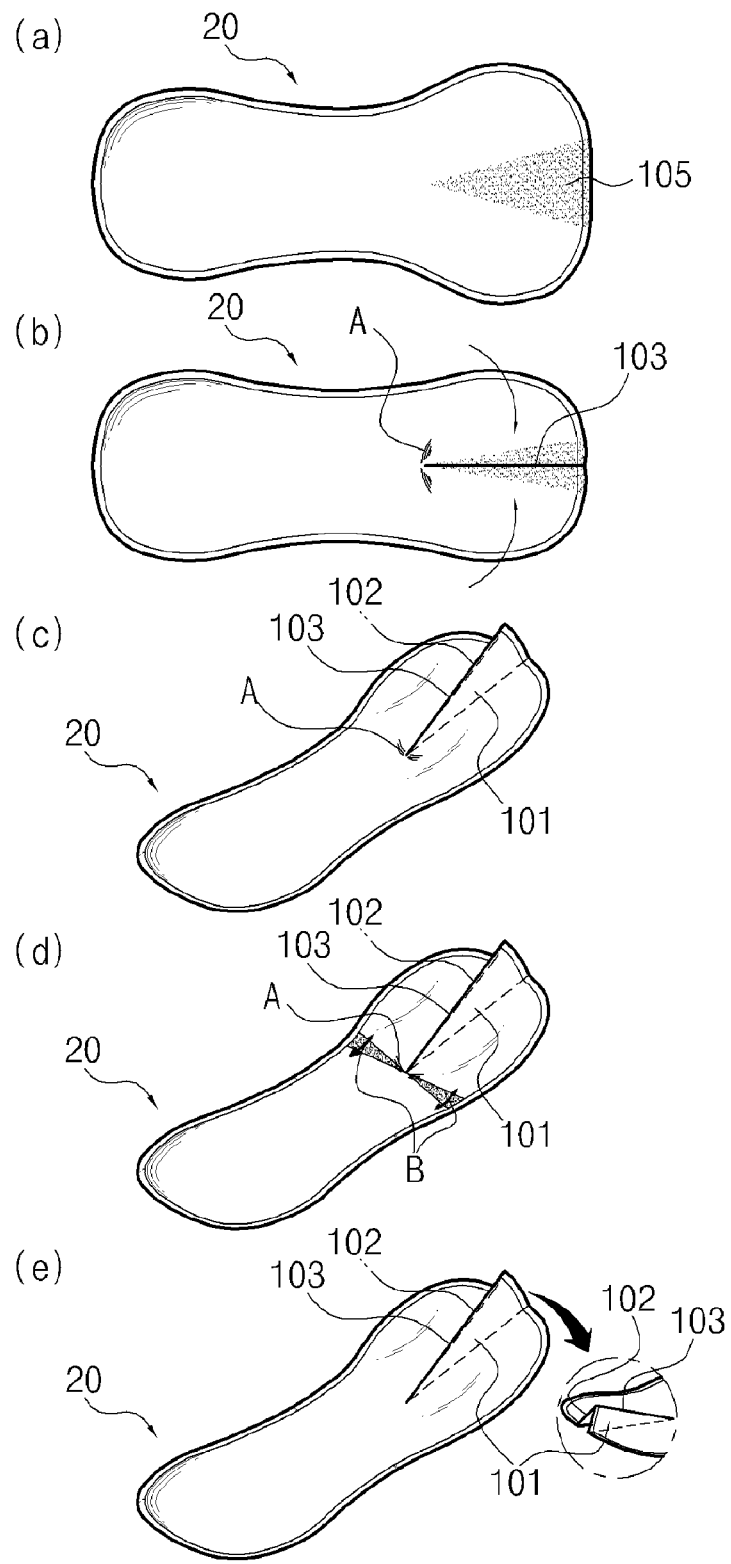

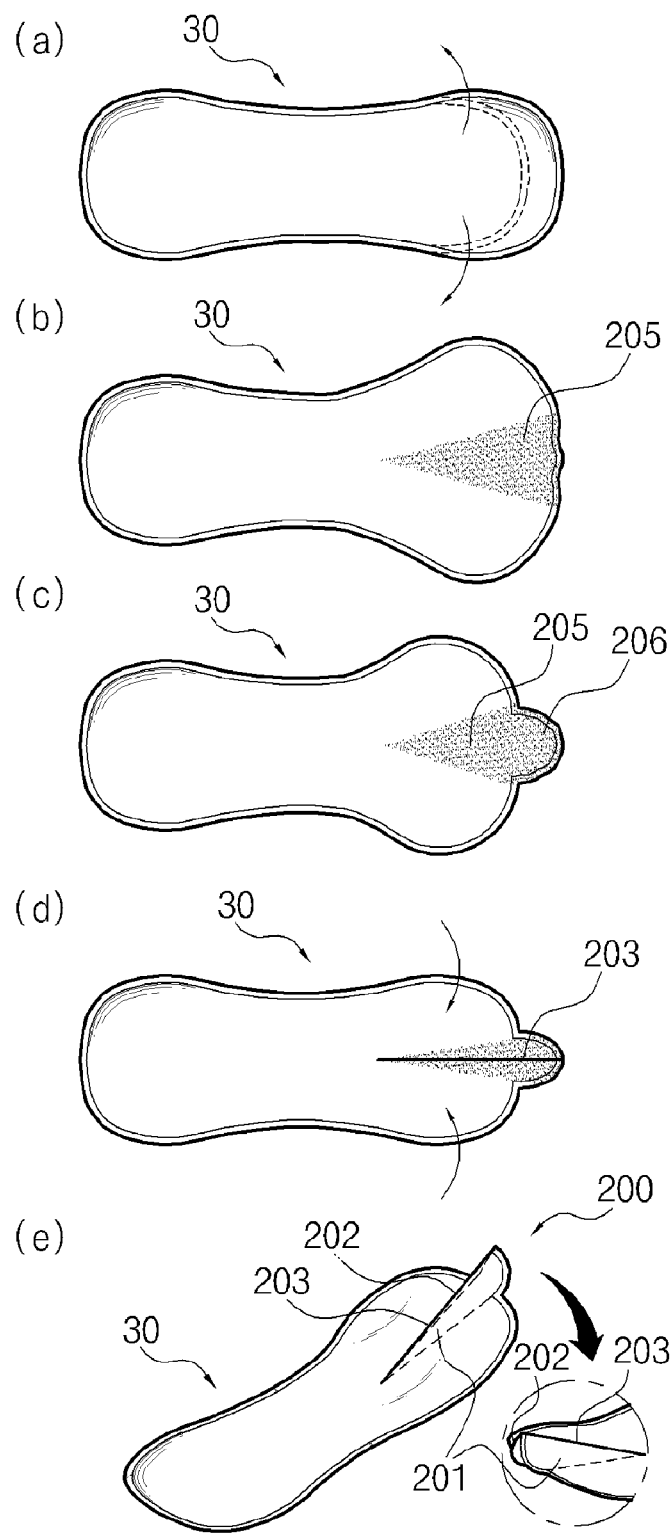
[Fig. 7]

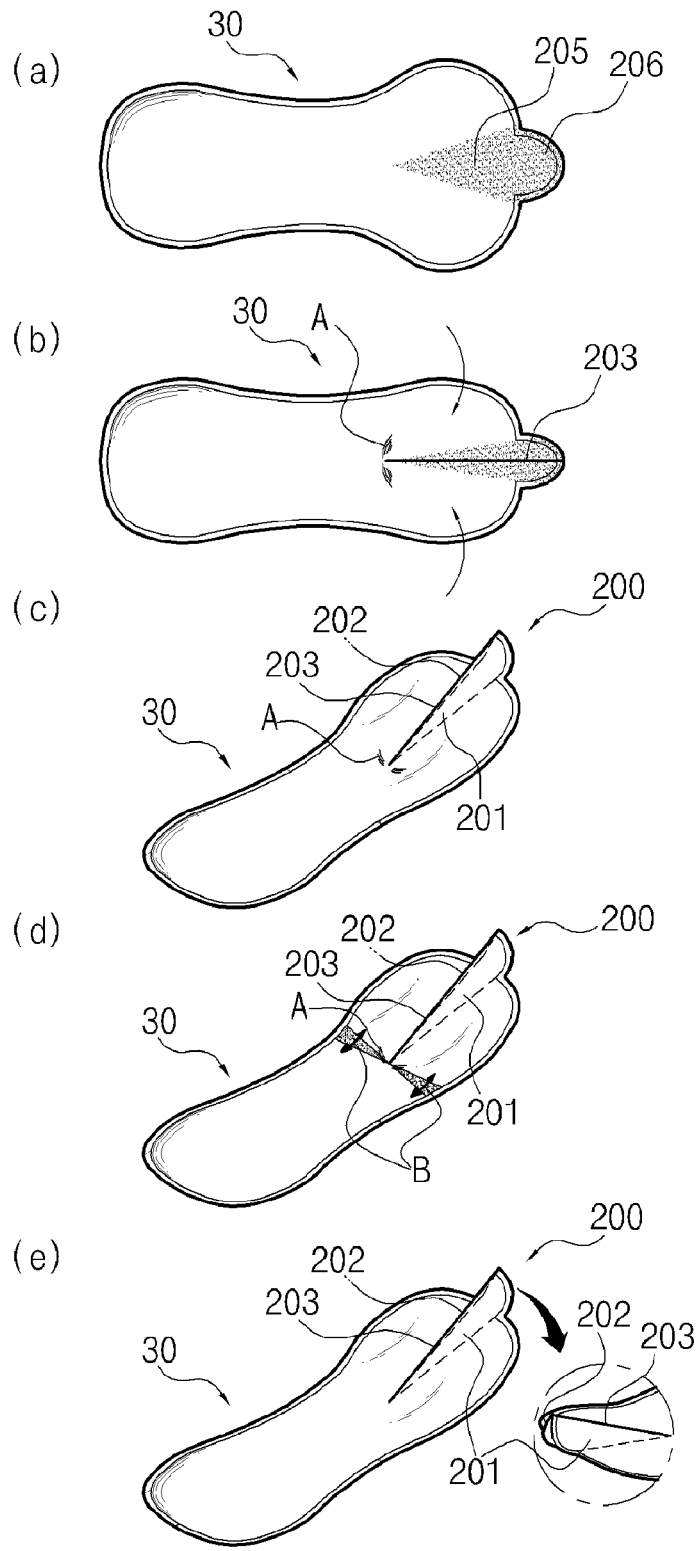
[Fig. 8]

HYGIENIC BAND HAVING THREE-DIMENSIONAL STRUCTURE AND MANUFACTURING METHOD THEREOF

TECHNICAL FIELD

The present invention relates, in general, to a hygienic band having a three-dimensional structure and a method of manufacturing the hygienic band and, more particularly, to a hygienic band having a three-dimensional structure and a method of manufacturing the hygienic band, in which a folded part forming a three-dimensional structure having a predetermined length is provided on a front end and/or a rear end along a central line of the hygienic band in a lengthwise direction thereof, thus preventing the leakage of menstrual blood when a user is active in the daytime or sleeps at night, and improving dressing style.

BACKGROUND ART

Generally, a hygienic band functions to absorb secretions, such as menstrual blood. In order to improve the material of the hygienic band to increase absorption ability and provide a good wearing sensation, and to satisfy a user's requirement according to the time that it is used, hygienic bands made of various materials and having various sizes, thicknesses, and shapes have been developed and come onto the market.

However, even though various kinds of hygienic bands have been developed, a user's dressing style is impeded compared to the style when not wearing the hygienic band, because the hygienic band is added to her underwear. In order to solve the problem, a tampon, as a substitute for the hygienic band, has come onto the market. However, since the tampon is inserted into the interior of the body, it is generally difficult for a virgin to use the tampon. Further, it has been reported that the tampon affects the health of a user, and thus women avoid using the tampon.

Further, in order to prevent menstrual blood from leaking to the back when a user's buttocks face the floor, such as when the user sleeps, an overnight hygienic band, which is longer than a general hygienic band, has come onto the market. Such an overnight hygienic band, having an extended length, prevents the leakage of menstrual blood to some extent during sleep. However, the conventional overnight hygienic band provides a poor wearing sensation due to the increased length, and thus a different hygienic band must be used when a user is active in the daytime.

Moreover, in the case of office ladies or students who must sit on a chair for a lengthy period of time, menstrual blood may leak to the back depending on the user's posture even when she is active in the daytime. If she takes excessive care to prevent such leakage, she may spend a lengthy period of time in a stationary position. This increases fatigue.

Therefore, the development of a hygienic band, which does not harm a woman wearer's health and does not impede dressing style, in addition to preventing menstrual blood from leaking to the front or back while the wearer is active in the daytime or sleeps at night, has been demanded.

DISCLOSURE OF INVENTION

Technical Problem

Accordingly, the present invention has been made keeping in mind the above problems occurring in the prior art, and an object of the present invention is to provide a hygienic band having a three-dimensional structure and a method of manufacturing the hygienic band, in which a folded part, forming a three-dimensional structure and inserted along a curved surface of a user's body, is provided on a rear end and/or a front end along a central line of the hygienic band in a lengthwise direction thereof, thus ensuring the user's good health, improving dressing style, and preventing menstrual blood from flowing to the front or back when she is active in the daytime or sleeps at night.

Technical Solution

In order to accomplish the object, the present invention provides a hygienic band having a three-dimensional structure and a pad having an absorbent layer and a cover for covering the absorbent layer, the hygienic band including a rear folded part provided at a central region on a rear portion of the pad, and having first and second folded surfaces, each having a shape of a triangle which is inclined such that a rear end thereof is higher. The rear folded part protrudes inwards in a shape of a triangular pyramid as the first and second folded surfaces are unfolded relative to a common oblique side and is inserted to be in close contact with a curved surface of a body, when the rear folded part is unfolded to wear the hygienic band.

Further, the hygienic band includes a front folded part provided at a central region on the front portion of the pad, and having third and fourth folded surfaces, each having a shape of a triangle which is inclined such that a front end thereof is higher. The front folded part protrudes inwards in a shape of a triangular pyramid as the third and fourth folded surfaces are unfolded relative to a common oblique side and is inserted to be in close contact with the curved surface of the body, when the front folded part is unfolded to wear the hygienic band.

In order to accomplish the object, the first embodiment of the present invention provides a method of manufacturing a hygienic band having a three-dimensional structure, including cutting cloth having an absorbent layer and a cover in a shape of a general pad front and rear portions of which have the same width; placing the cut cloth on a mold, the mold having a shape of the cut pad and having at a central region on a front and/or rear portion thereof a three-dimensional structure having a shape of a triangular pyramid which is inclined such that it is higher at an end thereof; forming a fan-shaped surplus portion at a central region on a front and/or rear portion of the cloth, by enlarging the front and/or rear portion of the cloth, cut according to the shape of the mold, in a direction from a center to left and right sides using external force; removing the mold from the cloth; and upwardly protruding the fan-shaped surplus portion formed on the cloth by exerting force in a direction from the left and right sides to the center, compressing the protruded surplus portion to form an edge, and pressing the protruded surplus portion against left and right surfaces relative to the edge, thus forming on the front and/or rear portion of the pad first and second folded surfaces, each having a shape of a triangle which is inclined such that it is higher at an end thereof.

Meanwhile, in order to accomplish the object, the second embodiment of the present invention provides a method of manufacturing a hygienic band having a three-dimensional structure, including placing a pattern on cloth having an absorbent layer and a cover, the pattern being formed such that a front and/or rear portion is further enlarged in a horizontal direction at a front and/or rear end, compared to a general pad; cutting the cloth along the pattern such that a fan-shaped surplus portion is provided on a front and/or rear portion of a pad, unlike the general pad front and rear portions of which have the same width; upwardly protruding the fan-shaped surplus portion formed on the cut cloth by exerting force in a direction from left and right sides to a center, compressing the protruded surplus portion to form an edge, and pressing the protruded surplus portion against left and right surfaces relative to the edge, thus forming on the front and/or rear portion of the pad first and second folded surfaces, each having a shape of a triangle which is inclined such that it is higher at an end; and smoothing out a wrinkled portion adjacent to a front and/or rear folded part having the first and second folded surfaces.

Advantageous Effects

As described above, a hygienic band according to the present invention has a three-dimensional structure created by a front and/or rear folded part, so that the hygienic band is naturally inserted to be in close contact with the curved surface of a wearer's body, that is, the crotch, thus highly efficiently preventing the leakage of menstrual blood which flows along the crotch when she is active in the daytime or sleeps, regardless of her posture. Further, a curved portion corresponding to the valley between left and right buttocks is naturally expressed, so that a user can have a good dressing style, like at normal times when she is not having her period, without affecting her health. The three-dimensional structure having the shape of a triangular pyramid is inserted into the crotch, so that the hygienic band naturally engages with the crotch. Such a structure secures the hygienic band to a predetermined position.

The method of manufacturing a hygienic band according to the present invention is advantageous in that it is easy to manufacture a folded part which is provided at a central region on a front and/or rear portion of the hygienic band, and has a three-dimensional structure so that the hygienic band is inserted into the crotch and is in contact with the curved portion of the crotch.

BRIEF DESCRIPTION OF THE DRAWINGS

FIGS. 1a and 1b are views showing a hygienic band having a three-dimensional structure, according to the first embodiment of the present invention, and FIG. 1c is a view showing the state where a folded part of the hygienic band according to the first embodiment rises up when a user wears the hygienic band;

FIGS. 2a and 2b are views showing a hygienic band having a three-dimensional structure, according to the second embodiment of the present invention, and FIG. 2c is a view showing the state where a folded part of the hygienic band according to the second embodiment rises up when a user wears the hygienic band;

FIGS. 3a and 3b are views showing a hygienic band having a three-dimensional structure, according to the third embodiment of the present invention, and FIG. 3c is a view showing the state where a folded part of the hygienic band according to the third embodiment rises up when a user wears the hygienic band;

FIG. 4a is a side view showing the hygienic band having the three-dimensional structure, according to the first embodiment of the present invention, and FIG. 4b is a rear view showing the state where the hygienic band having the three-dimensional structure, according to the first embodiment, is worn;

FIGS. 5a to 5d are views schematically showing a process of manufacturing a hygienic band having a three-dimensional structure, according to the first embodiment of the present invention;

FIGS. 6a to 6e are views showing a process of manufacturing a hygienic band having a three-dimensional structure, according to the second embodiment of the present invention;

FIGS. 7a to 7e are views showing a process of manufacturing a hygienic band having a three-dimensional structure, according to the third embodiment of the present invention; and FIGS. 8a to 8e are views showing a process of manufacturing a hygienic band having a three-dimensional structure, according to the fourth embodiment of the present invention.

BEST MODE FOR CARRYING OUT THE INVENTION

Hereinafter, the preferred embodiments of the present invention will be described in detail with reference to the accompanying drawings.

FIG. 1 shows a hygienic band having a three-dimensional structure, according to the first embodiment of the present invention.

As shown in FIG. 1a, the hygienic band having the three-dimensional structure according to the first embodiment of this invention includes a general pad 20 having an absorbent layer and a cover, and a rear folded part 100 which is provided at a central region on a rear portion R of the pad. Further, the rear folded part 100 is provided with first and second folded surfaces 101 and 102. Each of the first and second folded surfaces has the shape of a triangle which is inclined such that the height of the triangle is increased in a direction from a position on the pad to a rear end thereof.

When the hygienic band is unfolded so that a user can wear the hygienic band, as shown in FIG. 1c, the first and second folded surfaces are unfolded leftwards and rightwards relative to a common oblique side 103 corresponding to the junction of the first and second folded surfaces 101 and 102, and the first and second folded surfaces protrude to the inside of the pad in the shape of the triangular pyramid. The first and second folded surfaces are inserted along the rear portion of the crotch, so that the hygienic band is in close contact with the user's body. In this case, the term "crotch" denotes a valley region which is concavely formed between the left and right buttock muscles.

Meanwhile, according to the first embodiment, the common oblique side 103 of the first and second folded surfaces 101 and 102 may be rounded gently upwards so that the hygienic band is in more extensive contact with a user's crotch. As such, the example where the common oblique side 103 of the first and second folded surfaces 101 and 102, having the triangular shape, is rounded is shown in FIG. 1b.

According to the first embodiment, the rear folded part 100 and the common oblique side 103 of the triangular first and second folded surfaces 101 and 102 forming the rear folded part 100 may be manufactured to have various lengths, inclination angles and curvatures, according to the user's body type.

For example, assuming that the pad is folded in three stages in the lengthwise direction of the pad, that is, the pad is divided into a front portion, a middle portion, and a rear portion, the rear folded part 100 may be formed to extend from the start point of the rear portion to the rear end of the pad. Further, the rear folded part 100 may be formed to extend from a center of the middle portion to the rear end of the pad.

FIG. 2 shows the construction of a hygienic band having a three-dimensional structure, according to the second embodiment of the present invention.

As shown in FIG. 2a, the hygienic band according to the second embodiment is constructed so that first and second folded surfaces 201 and 202 of a rear folded part 200 protrude from the rear end of a pad to a predetermined position, unlike the hygienic band having the three-dimensional structure of the first embodiment.

When the hygienic band is unfolded so that a user wears the hygienic band, as shown in FIG. 2c, the first and second folded surfaces 201 and 202 protruding rearwards from the pad are unfolded leftwards and rightwards relative to a common oblique side 203 corresponding to the junction of the first and second folded surfaces 201 and 202. Further, the first and second folded surfaces 201 and 202 protrude to the inside of the pad in the shape of a triangular pyramid, and are inserted into the rear portion of the crotch. Thereby, the hygienic band is in close contact with the user's body, and the first and second folded surfaces 201 and 202 of the extended rear portion extend further to the rear of the crotch. Such an extended structure can more efficiently prevent the leakage of menstrual blood along the crotch.

According to the second embodiment, the oblique side 203 of the first and second folded surfaces 201 and 202 may be rounded gently upwards so that the hygienic band is inserted into a user's crotch to be in closer contact with the curved portion of the crotch. As such, the example where the common oblique side 203 of the first and second folded surfaces 201 and 202 is rounded is shown in FIG. 2b.

FIG. 3 shows the construction of a hygienic band having a three-dimensional structure, according to the third embodiment of the present invention.

As shown in FIG. 3a, the hygienic band according to the third embodiment comprises a general-type pad having an absorbent layer and a cover. According to the third embodiment, a rear folded part 100 is provided on the rear portion R of the pad 20 along a central line thereof, and in addition, a front folded part 300 is provided on a front portion F of the pad 20 along the central line thereof. Similar to the first embodiment, the rear folded part 100 is provided with first and second folded surfaces 101 and 102. Each of the first and second folded surfaces has the shape of a triangle which is inclined such that the height of the triangle is increased in a direction from a position on the pad to a rear end thereof. Further, the front folded part 300 is provided with third and fourth folded surfaces 301 and 302. Each of the third and fourth folded surfaces has the shape of a triangle which is inclined such that the height of the triangle is increased in a direction from a position on the pad to a front end thereof.

As shown in FIG. 3c, when the hygienic band according to the third embodiment is unfolded so that a user can wear the hygienic band, the first and second folded surfaces of the rear folded part 100 are unfolded leftwards and rightwards relative to a common oblique side 103 corresponding to the junction of the first and second folded surfaces 101 and 102. Further, the first and second folded surfaces protrude to the inside of the pad in the shape of a triangular pyramid, and are inserted into the rear portion of the crotch. Thereby, the hygienic band is in close contact with the user's body. Meanwhile, the third and fourth folded surfaces of the front folded part 300 are unfolded leftwards and rightwards relative to a common oblique side 303 corresponding to the junction of the third and fourth folded surfaces 301 and 302. Further, the third and fourth folded surfaces protrude to the inside of the pad in the shape of a triangular pyramid, and are inserted into the front portion of the crotch. Thereby, the hygienic band is in close contact with the user's body.

Meanwhile, in the third embodiment, the common oblique side 103 of the first and second folded surfaces 101 and 102 and the common oblique side 303 of the third and fourth folded surfaces 301 and 302 may also be rounded gently upwards so that the hygienic band is in closer contact with the curved portion of a user's crotch. The example where the common oblique side 103 of the first and second folded surfaces 101 and 102 and the common oblique side 303 of the third and fourth folded surfaces 301 and 302 are rounded is shown in FIG. 3b.

Further, according to the third embodiment, the front and rear folded parts 300 and 100, the common oblique side 303 of the triangular third and fourth folded surfaces 301 and 302 forming the front folded part 300, and the common oblique side 103 of the triangular first and second folded surfaces 101 and 102 forming the rear folded part 100 may have various lengths, inclination angles, and curvatures. Further, the first and second folded surfaces 101 and 102 of the rear folded part 100 may protrude rearwards from the rear end of the pad to a predetermined length, as in the second embodiment. As necessary, the third and fourth folded surfaces 301 and 302 of the front folded part 300 may protrude forwards from the front end of the pad to a predetermined length.

FIG. 4a is a side view showing the hygienic band having the three-dimensional structure, according to the first embodiment of the present invention, and FIG. 4b is a rear view showing the state where the hygienic band is worn. The operational effect of the hygienic band having the three-dimensional structure according to the present invention will be described with reference to FIG. 4.

As shown in the drawing, when the hygienic band having the three-dimensional structure according to the present invention is worn, the rear folded part 100 forms a three-dimensional structure having the shape of a triangular pyramid which is inserted in a user's crotch (+z-axis direction), and is inserted in the lengthwise direction (±y-axis direction) of the crotch to be in close contact with the crotch. Hence, menstrual blood flowing along the crotch is immediately absorbed by the first and second folded surfaces 101 and 102 of the rear folded part, and thus even small leakage of the menstrual blood can be prevented.

Further, the rear folded part 100 of the invention is manufactured in the method according to the first to fourth embodiments which will be described later, and protrudes inwards in the shape of the triangular pyramid when the hygienic band is worn. Thus, the rear folded part is naturally inserted along the curved surface of the rear portion of the crotch without being wrinkled, so that the hygienic band is in close contact with the body. That is, the three-dimensional structure created by the rear folded part rises up to correspond to the shape of the curved surface of the body. When the hygienic band is worn, the protruding portion of the inner surface of the pad is naturally inserted into the rear portion of the crotch and thus is in close contact with the crotch. Thus, the curved portion of the body can be naturally expressed through the outer surface of the pad. Therefore, when a user puts on pants or the like, a good dressing style is realized without impediment, just as when she is not having her period. Further, the triangular-pyramid-shaped three-dimensional structure defined by the rear folded part is inserted into the crotch, and engages with the crotch, thus functioning to secure the hygienic band to a predetermined position.

The operational effect of the first embodiment has been described hereinbefore. Since it is apparent that the hygienic band according to the second or third embodiment improves a user's dressing style, prevents the leakage of menstrual blood flowing along the front or rear portion of the crotch, and is held to a predetermined position, the detailed operational effect of the second or third embodiment will be omitted.

Especially, when the rear folded part extending to the buttocks is provided on the rear portion of the pad, as in the second embodiment, the hygienic band can more efficiently prevent menstrual blood from leaking along the crotch to the buttocks, without affecting dressing style. Further, in the first to third embodiments, when the common oblique side 103, 203, or 303, corresponding to a portion inserted into the curved valley portion of the user's body, is rounded, the hygienic band can be inserted into the curved portion of the body to be in closer contact with the curved portion. When the hygienic band is worn, the depressed shape of the rounded oblique side 103, 203, or 303 is exhibited at the outer surface of the pad. Thus, a restricted feeling which is caused by the pressure of a garment when a user puts on the outer garment, such as pants, can be reduced due to the depressed shape of the rounded oblique side. Further, a better dressing style is achieved because the rounded oblique side has a curve similar to that of the garment.

FIGS. 5 to 8 illustrate the process of manufacturing the hygienic band, according to the present invention. The drawings show the process of forming the rear folded part. However, since the process of forming the rear folded part may be applied to the process of forming the front folded part, the hygienic band additionally having the front folded part will be described with reference to the drawings.

The method of manufacturing the hygienic band having the three-dimensional structure according to the present invention includes a step of preparing cloth having a surplus portion for forming the folded part at the front and/or rear portion of the pad, and a step of forming the folded part using the surplus portion.

First, according to the first embodiment, in order to manufacture cloth having the surplus portion for forming the folded part at the central region on the front and/or rear portion of the pad, a mold, which has the shape of a general pad and has the three-dimensional structure having the shape of a triangular pyramid that is inclined upwards in a direction from a position on the pad to the front or rear end thereof, is prepared.

In a detailed description, when the hygienic band having the three-dimensional structure according to the first embodiment is manufactured, the cloth consisting of the absorbent layer and the cover is cut in the shape of a general pad 20 front and rear portions of which are the same width (see, FIG. 5a). Thereafter, the cut cloth is placed on the mold with the three-dimensional structure having the shape of the triangular pyramid that is inclined upwards in a direction from a position on the pad to the front or rear end thereof.

Next, the front and/or rear portion of the cloth is enlarged in the direction from the center of the cloth to the left and right ends thereof by an external force, according to the shape of the mold. Thereby, a fan-shaped surplus portion 105 is formed on the front and/or rear portion of the cloth (see, FIG. 5b). That is, the central area of the front and/or rear portion of the cloth is enlarged according to the triangular-pyramid-shaped three-dimensional structure of the mold using a machine, such as a press. Thereby, the fan-shaped surplus portion 105 for forming the three-dimensional folded part is provided on the front and/or rear portion of the cloth. Meanwhile, by pressing a depressed mold, having the same shape as the mold, against the mold having the three-dimensional structure of the triangular pyramid shape, the fan-shaped surplus portion may be formed on the front and/or rear portion of the cloth.

Next, after the mold is removed from the cloth, the fan-shaped surplus portion 105 is protruded upwards by force acting in the direction from left and right sides to the center of the front and/or rear portion of the pad, and is compressed, thus forming an edge 103 along the central line of the surplus portion 105 (see, FIG. 5c). In such a state, the protruding surplus portion 105 is pressed against the left and right sides of the pad relative to the edge 103. Thereby, the first and second folded surfaces 101 and 102, each having the shape of a triangle which is inclined upwards in a direction from a position of the front and/or rear portion of the pad to an end thereof, are formed (see, FIG. 5d). In this way, the front and/or rear folded part of the hygienic band having the three-dimensional structure is formed.

In the first embodiment, when the front and/or rear folded part of the pad is formed using a mold having a line portion of the triangular pyramid which is rounded gently upwards along the corresponding curved portion of the body when the hygienic band is worn, an additional rounding operation, which will be described later, is not required.

Further, as in the second embodiment shown in FIG. 6, a pattern, such as a paper pattern, the front and rear ends of which are wider than those of the general pad, may be used to provide a surplus portion for forming a folded part at a central region on the front and/or rear portion of the pad.

That is, as shown in FIG. 6, according to the second embodiment, the pattern is placed on cloth consisting of an absorbent layer and a cover. The cloth is cut along the pattern. In this case, a fan-shaped surplus portion 105 is provided on the front and/or rear portion of the pad, unlike the general pad, front and rear portions of which have the same width (see, FIG. 6a). Further, the fan-shaped surplus portion provided on the cut cloth is pushed in a direction from left and right sides of the pad to the center thereof by an external force. Thereby, the fan-shaped surplus portion is protruded upwards and is compressed, so that an edge is formed along the central line of the surplus portion (see, FIG. 6b). In such a state, the protruding surplus portion is pressed against the left and right surfaces relative to the edge. Thereby, the first and second folded surfaces, each having the shape of a triangle which is inclined upwards in a direction from a position of the front and/or rear portion of the pad to an end thereof, are formed (see, FIG. 6c). The process is the same as the first embodiment.

Unlike the first embodiment, according to the second embodiment, after the front and/or rear folded part having the first and second folded surfaces is formed, the operation of smoothing out a wrinkled portion A which is adjacent to the front and/or rear folded part is added by applying a force on the left and right areas of the fan-shaped surplus portion relative to a start point of the front and/or rear folded part, in direction B (see, FIGS. 6d and 6e). Such an operation allows the start point of the front and/or rear folded part to be in close contact with the curved portion of the body without being wrinkled when the front and/or rear folded part protrudes inwards in the form of the triangular pyramid.

Further, in the first and second embodiments, the operation of forming the first and second folded surfaces may further include the operation of upwardly rounding the edge 103, formed on the central line of the front and/rear folded part, according to the corresponding curved portion of the body when the hygienic band is worn.

Meanwhile, the method of manufacturing a hygienic band having a three-dimensional structure and an extended rear folded part, according to the third and fourth embodiments of the present invention, is shown in FIGS. 7 and 8. That is, the manufacturing method of the third embodiment includes the operation of forming a folded part at a central region on the front and/or rear portion of a pad using a mold, as in the first embodiment. The manufacturing method of the fourth embodiment includes the operation of forming a folded part using a pattern, as in the second embodiment.

As shown in FIG. 7, according to the third embodiment, cloth is cut so that a rear portion is extended in the lengthwise direction of a pad, compared to the pad having a general length (see, FIG. 7a). Steps other than the cutting step are equal to those of the first embodiment. That is, the cut cloth is placed on the mold, and the front and/or rear portion of the cloth, which is cut according to the shape of the mold, is enlarged in a direction from the center of the pad to left and right sides thereof by an external force. Thereby, a fan-shaped surplus portion 205 is provided on at a central region on the front and/or rear portion of the cloth (see, FIG. 7b). Next, the mold is removed from the cloth.

According to the third embodiment, the cut cloth is shaped such that the rear portion thereof is extended in a lengthwise direction, compared to the pad of a general length. Thus, the mold has a shape corresponding to the shape of the cut pad, and has on a front or rear portion thereof the three-dimensional structure having the shape of the triangular pyramid which is inclined upwards in a direction from a position on the pad to an end thereof. In this case, the three-dimensional structure of the rear portion is extended by the length of the extended rear portion. Thus, the fan-shaped surplus portion, formed on the rear portion of the cloth along a central line thereof, has a shape 205 with a rear portion extended in proportion to the length of the extended rear portion.

Next, the first and second folded surfaces are formed on the front and/or rear portion of the pad. At this step, the extended portion of the rear portion of the pad is cut such that a semi-elliptical protruding part 206 is extended from the center of the rear end, unlike the pad of a general length. In this case, the semi-elliptical protruding part 206 is provided on the fan-shaped surplus portion 205 of the cloth (see, FIG. 7c). Steps other than the above-mentioned steps are equal to those of the first embodiment. That is, an edge 203 is formed along the central line of the fan-shaped surplus portion 205 and the protruding part 206 (see, FIG. 7d), and the left and right surfaces relative to the edge are pressed, so that the triangular first and second folded surfaces 201 and 202 are formed (see, FIG. 7e).

According to this embodiment, after the elliptical protruding part 206 is formed using the fan-shaped surplus portion, the edge 203 is formed along the central line of the fan-shaped surplus portion. Thereafter, the first and second folded surfaces 201 and 202 are formed. However, unlike the sequence of this embodiment, the operation of forming the elliptical protruding part may be conducted after the first and second folded surfaces 201 and 202 have been formed.

Meanwhile, as shown in FIG. 8, the manufacturing method of a hygienic pad according to the fourth embodiment forms a fan-shaped surplus portion using a pattern. The pattern is shaped such that an end of a front and/or rear portion is enlarged in a horizontal direction compared to the general pad, and a semi-elliptical protruding part extends from the center of the rear end of the pad.

By cutting the cloth along the pattern, a fan-shaped surplus portion 205 is formed on the front and/or rear portion of a pad 30, and a protruding part 206 is formed to extend from the center of the rear end of the pad in a semi-elliptical shape (see, FIG. 8a). Steps other than this step are equal to those of the second embodiment. That is, an edge 203 is formed along the central line of the fan-shaped surplus portion 205 and the protruding part 206 (see, FIG. 8b), and left and right surfaces relative to the edge are pressed, so that triangular first and second folded surfaces 201 and 202 are formed (see, FIG. 8c). Further, force acts on the left and right sides of the fan-shaped area in direction B from the start point of the front and/or rear folded part having the first and second folded surfaces 201 and 202, so that the left and right sides of the fan-shaped area are enlarged. Thereby, a wrinkled portion A adjacent to the front and/or rear folded part is smoothed out (see, FIGS. 8d and 8e).

The manufacturing method of the hygienic band according to the third and fourth embodiments provides the three-dimensional structure, extending rearwards to be in close contact with a wearer's buttocks, to the rear portion of the pad, thus more efficiently preventing menstrual blood from leaking to the back along her crotch, without affecting her dressing style.

The manufacturing method of the hygienic band according to the first to fourth embodiments adopts the method using the mold, the paper pattern, etc. so as to form the folded part at the central region on the front and/or rear portion of the hygienic band. However, the invention may use other methods, as long as the surplus portion for forming the folded part is provided on the front and/or rear portion of the pad.

As such, the operation of forming the surplus portion on the front and/or rear portion of the pad may be applied to the case where a portion for forming the surplus portion is made of pliant cloth, such as cotton or a cotton blend. However, the invention is not limited to such material. That is, as long as the cloth can form the surplus portion on the front and/or rear portion of the pad and the folded part is formed using the surplus portion, any cloth may be used. Since the folded part for forming the three-dimensional structure is made using the surplus portion, the hygienic band having the three-dimensional structure may be manufactured to be entirely flat without the surroundings of the folded part being wrinkled. Further, when the hygienic band is worn, the hygienic band forms a smooth curved shape corresponding to the curved portion of the body, without a protruding portion.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A hygienic band having a three-dimensional structure and a pad having an absorbent layer and a cover for covering the absorbent layer, the hygienic band comprising:
    a rear folded part provided at a central region on a rear portion of the pad, and having first and second folded surfaces, each having a shape of a triangle which is inclined such that a rear end thereof is higher, the rear folded part protruding inwards in a shape of a triangular pyramid as the first and second folded surfaces are unfolded relative to a common oblique side and being inserted along a rear portion of a crotch of a body to be in close contact with a curved surface of the body, when the rear folded part is unfolded to wear the hygienic band,
    wherein the common oblique side has a shape of line, and
    wherein the first folded surface and the second folded surface are connected to each other by the common oblique side, without having an adhesive material interposed between the first and second folding surfaces.

2. The hygienic band according to claim 1, wherein the first and second surfaces of the rear folded part extend from a rear end of the pad in such a way as to protrude a predetermined length.

3. The hygienic band according to claim 2, wherein the common oblique side of the first and second folded surfaces has a shape of line that is rounded upwards to correspond to a curved line of the body.

4. The hygienic band according to claim 3, wherein the rear folded part extends from a start point of the rear portion to the rear end of the pad, when the pad is divided into three portions, including a front portion, a middle portion, and the rear portion.

5. The hygienic band according to claim 2, further comprising:
a front folded part provided at a central region on a front portion of the pad, and having third and fourth folded surfaces, each having a shape of a triangle which is inclined such that a front end thereof is higher, the front folded part protruding inwards in a shape of a triangular pyramid as the third and fourth folded surfaces are unfolded relative to a common oblique side and being inserted to be in close contact with the curved surface of the body, when the front folded part is unfolded to wear the hygienic band.

6. The hygienic band according to claim 5, wherein the common oblique side of the first and second folded surfaces and the common oblique side of the third and fourth folded surfaces are rounded upwards to correspond to the curved line of the body.

7. The hygienic band according to claim 1, wherein the common oblique side of the first and second folded surfaces has a shape of line that is rounded upwards to correspond to a curved line of the body.

8. The hygienic band according to claim 7, wherein the rear folded part extends from a start point of the rear portion to the rear end of the pad, when the pad is divided into three portions, including a front portion, a middle portion, and the rear portion.

9. The hygienic band according to claim 1, further comprising:
a front folded part provided at a central region on a front portion of the pad, and having third and fourth folded surfaces, each having a shape of a triangle which is inclined such that a front end thereof is higher, the front folded part protruding inwards in a shape of a triangular pyramid as the third and fourth folded surfaces are unfolded relative to a common oblique side and being inserted to be in close contact with the curved surface of the body, when the front folded part is unfolded to wear the hygienic band.

10. The hygienic band according to claim 9, wherein the common oblique side of the first and second folded surfaces and the common oblique side of the third and fourth folded surfaces are rounded upwards to correspond to the curved line of the body.

11. A method of manufacturing a hygienic band having a three-dimensional structure, comprising:
cutting cloth having an absorbent layer and a cover in a shape of a general pad front and rear portions of which have the same width;
placing the cut cloth on a mold, the mold having a shape of the cut pad and having at a central region on a rear portion thereof a three-dimensional structure having a shape of a triangular pyramid which is inclined such that it is higher at an end thereof;
forming a fan-shaped surplus portion at a central region on a rear portion of the cloth, by enlarging the rear portion of the cloth, cut according to the shape of the mold, in a direction from a center to left and right sides using external force;
removing the mold from the cloth; and
upwardly protruding the fan-shaped surplus portion formed on the cloth by exerting force in a direction from the left and right sides to the center, compressing the protruded surplus portion to form an edge, and pressing the protruded surplus portion against left and right surfaces relative to the edge, thus forming a rear folded part provided at the rear portion of the pad and having first and second folded surfaces, each having a shape of a triangle which is inclined such that a rear end thereof is higher, the rear folded part protruding inwards in a shape of a triangular pyramid as the first and second folded surfaces are unfolded relative to the edge and being inserted along a rear portion of a crotch of a body to be in close contact with a curved surface of the body, when the rear folded part is unfolded to wear the hygienic band, wherein the edge has a shape of line,
wherein the first folded surface and the second folded surface are connected to each other by the edge, without having an adhesive material interposed between the first and second folding surfaces.

12. The method according to claim 11, wherein
the cloth is cut in the shape of the general pad front and rear portions of which have the same width, and is cut such that a rear portion thereof is extended in a lengthwise direction, compared to a pad having a general length, and
the forming the rear folded part having the first and second folded surfaces comprises cutting the rear portion extended in the lengthwise direction such that a semi-elliptical protruding part extends from a center of a rear end of the pad having the general length, the protruding part being formed on the fan-shaped surplus portion.

13. The method according to claim 12, wherein the forming the rear folded part having the first and second folded surfaces further comprises upwardly rounding the edge, formed along a central line of the first and second folded surfaces, to correspond to a curved line of a body.

14. The method according to claim 11, wherein the forming the rear folded part having the first and second folded surfaces further comprises upwardly rounding the edge, formed along a central line of the first and second folded surfaces, to correspond to a curved line of a body.

15. A method of manufacturing a hygienic band having a three-dimensional structure, comprising:
placing a pattern on cloth having an absorbent layer and a cover, the pattern being formed such that a rear portion is further enlarged in a horizontal direction at a front and/or rear end, compared to a general pad;
cutting the cloth along the pattern such that a fan-shaped surplus portion is provided on a rear portion of a pad, unlike the general pad front and rear portions of which have the same width;
upwardly protruding the fan-shaped surplus portion formed on the cut cloth by exerting force in a direction from left and right sides to a center, compressing the protruded surplus portion to form an edge, and pressing the protruded surplus portion against left and right surfaces relative to the edge, thus forming a rear folded part provided at the rear portion of the pad and having first and second folded surfaces, each having a shape of a triangle which is inclined such that a rear end thereof is higher, the rear folded part protruding inwards in a shape of a triangular pyramid as the first and second folded surfaces are unfolded relative to the edge and being inserted along a rear portion of a crotch of a body to be in close contact with a curved surface of the body, when the rear folded part is unfolded to wear the hygienic band, wherein the edge has a shape of line; and
smoothing out a wrinkled portion adjacent to the rear folded part having the first and second folded surfaces, wherein the first folded surface and the second folded surface are connected to each other by the edge, without having an adhesive material interposed between the first and second folding surfaces.

16. The method according to claim 15, wherein the forming the rear folded part having the first and second folded surfaces further comprises upwardly rounding the edge, formed along a central line of the first and second folded surfaces, to correspond to a curved line of a body.

17. A method of manufacturing a hygienic band having a three-dimensional structure, comprising:

placing a pattern on cloth having an absorbent layer and a cover, the pattern being formed such that a rear portion is further enlarged in a horizontal direction at a rear end, compared to a general pad, and a semi-elliptical protruding part extends from a center of a rear end of a pad;

cutting the cloth along the pattern such that a fan-shaped surplus portion is provided on a rear portion of a pad, and a semi-elliptical protruding part extends from the center of the rear end of the pad, unlike the general pad front and rear portions of which have the same width;

upwardly protruding the fan-shaped surplus portion and the protruding part formed on the cut cloth by exerting force in a direction from left and right sides to a center, compressing the protruded surplus portion to form an edge, and pressing the fan-shaped surplus portion and the protruding part against left and right surfaces relative to the edge, thus forming a rear folded part provided at the rear portion of the pad and having first and second folded surfaces, each having a shape of a triangle which is inclined such that a rear end thereof is higher, the rear folded part protruding inwards in a shape of a triangular pyramid as the first and second folded surfaces are unfolded relative to the edge and being inserted along a rear portion of a crotch of a body to be in close contact with a curved surface of the body, when the rear folded part is unfolded to wear the hygienic band, wherein the edge has a shape of line; and smoothing out a wrinkled portion adjacent to a front and/or rear folded part having the first and second folded surfaces, wherein the first folded surface and the second folded surface are connected to each other by the edge, without having an adhesive material interposed between the first and second folding surfaces.

18. The method according to claim 17, wherein the forming the rear folded part having the first and second folded surfaces further comprises upwardly rounding the edge, formed along a central line of the first and second folded surfaces, to correspond to a curved line of a body.

* * * * *